United States Patent [19]
Imai et al.

[11] Patent Number: 5,955,529
[45] Date of Patent: Sep. 21, 1999

[54] BIODEGRADABLE MATERIAL AND PROCESS FOR THE PREPARATION THEREOF

[75] Inventors: Yoji Imai; Yasutoshi Kakizawa; Masao Kamikura; Toshiki Shikata, all of Chiba, Japan

[73] Assignee: Dainippon Ink and Chemicals, Inc., Tokyo, Japan

[21] Appl. No.: 08/897,140

[22] Filed: Jul. 21, 1997

[30] Foreign Application Priority Data

Jul. 23, 1996 [JP] Japan .................................. 8-193364

[51] Int. Cl.$^6$ ..................................................... C08F 20/00
[52] U.S. Cl. ............................................. 524/417; 528/272
[58] Field of Search ............................... 524/417; 528/272

[56] References Cited

U.S. PATENT DOCUMENTS

| | | | |
|---|---|---|---|
| 4,698,375 | 10/1987 | Dorman et al. ......................... | 523/115 |
| 5,552,454 | 9/1996 | Kretschmann et al. ................. | 523/113 |

*Primary Examiner*—Ana Woodward
*Attorney, Agent, or Firm*—Armstrong, Westerman, Hattori, McLeland & Naughton

[57] ABSTRACT

The present invention provides a biodegradable material having excellent organic compatibility, moldability, mechanical properties, biodegradability and storage stability which can be used as bone substitute material, material for osteosynthesis, bone filling material, dental material, material having controlled release of chemical, material having controlled release of physiologically active compound or the like and a process for the preparation thereof. A novel biodegradable material is provided, comprising as essential components a lactic acid-based polymer (A) consisting of structural units (a) derived from lactic acid components and polyester structural units (b) derived from dicarboxylic acid components and diol components, the weight ratio of (a)/(b) being from 98/2 to 20/80, and a calcium phosphate-based compound (B), wherein the weight ratio of (A)/(B) is from 99/1 to 30/70. A process for the preparation of such a biodegradable material is also provided.

2 Claims, No Drawings

BIODEGRADABLE MATERIAL AND PROCESS FOR THE PREPARATION THEREOF

FIELD OF THE INVENTION

The present invention relates to a biodegradable material having excellent formability, mechanical properties and biodegradability useful as bone substitute materials, materials for osteosynthesis, bone filling materials, dental materials, controlled chemical release materials, materials having controlled release of physiologically active compound, etc.

BACKGROUND OF THE INVENTION

As restorative materials for mending the defect of bone such as maxillary bone and biodegradable materials used as pins for osteosynthesis at a bone fracture there are disclosed biodegradable polymers such as polylactic acid, polyglycolic acid and polycaprolactam and copolymers thereof in JP-A-5-42202 (The term "JP-A" as used herein means an "unexamined published Japanese patent application") and JP-A-5-309103.

The materials disclosed in the above cited patents are biodegradable, but their biodegradability can normally be hardly controlled. These polymers are also disadvantageous in that the enhancement of biodegradability requires the reduction of their molecular weight that deteriorates the mechanical properties thereof and hence causes a practical problem.

These biodegradable polymers are further disadvantageous in that their biodegradability is accelerated with time, causing the rise in the internal acidity thereof that tends to result eventually in the inflammation of the embedded site. These biodegradable polymers are further disadvantageous in that fibrous tissues or osseous tissues can hardly be induced into and regenerated at the site where they have been decomposed.

The complexing of a polylactic acid with hydroxyapatite or tricalcium phosphate in molten state is disclosed in JP-A-63-89166. A composite of an oligomer of lactic acid and/or glycolic acid with calcium phosphate is disclosed in JP-A-4-500013.

However, the complexing of a polylactic acid with hydroxyapatite or tricalcium phosphate in molten state is disadvantageous in that these materials can hardly be kneaded with each other, resulting in the production of a heterogeneous composite which can be hardly reproduced. Further, since a polylactic acid normally has a poor thermal stability, it is liable to drastic drop of molecular weight during melting, resulting in the production of a composite having a low elastic modulus and insufficient flexural strength and other physical properties. The application of such a composite is relatively restricted.

Referring to the composite of an oligomer of lactic acid and/or glycolic acid with calcium phosphate, the two components can be better kneaded with each other. However, the composite thus obtained has a molecular weight as low as from about 200 to 10,000. Therefore, the composite exhibits a low mechanical strength and an insufficient elastic modulus and thus can hardly be put into practical use.

JP-A-4-279520 discloses chemical-releasing preparations obtained by a process which comprises compression-molding a chemical and a polymer such as lactic acid and glycolic acid or copolymer thereof, or melting these materials and then molding the mixture, and chemical-releasing preparations obtained by a process which comprises granulating the chemical-releasing preparations, mixing the preparations with a calcium phosphate-based compound such as hydroxyapatite and $\beta$-tricalcium phosphate, and then compression-molding the mixture.

JP-A-6-298639 discloses spherical chemical-releasing preparations obtained by molding a composite of a chemical with a polymer such as lactic acid, glycolic acid and lactone or copolymer thereof and a calcium phosphate-based compound such as hydroxyapatite and $\beta$-tricalcium phosphate in a laminated structure having different amounts of chemical and chemical-releasing preparations obtained by expanding the chemical-releasing preparations with a blowing agent.

However, these chemical-releasing preparations are disadvantageous in that their biodegradation rate is accelerated with time, making it difficult to control the biodegradation thereof. These chemical-releasing preparations must be capable of gradually releasing a chemical as well as must have an affinity for tissue. Further, these chemical-releasing preparations must be flexible when applied to muscle, etc. Moreover, if surgically embedded in the living body, these chemical-releasing preparations are preferably not needed to be taken out therefrom.

The addition of calcium phosphate to a polylactic acid makes it possible to a gradually releasable chemical which exhibits a high affinity for tissue and doesn't need to be taken out. However, as the added amount of the calcium phosphate-based compound increases, the kneading of these components becomes more difficult and the resulting preparations show a lower flexibility. In the case where a known lactic acid-based copolymer with glycolic acid or the like is used, if the content of calcium phosphate is increased, the resulting material exhibits an insufficient strength.

Further, the polylactic acid, copolymer thereof or composite thereof with a calcium phosphate-based compound disclosed in the above cited patents normally has a great content of a residual lactide derived from polylactic acid. The residual lactide undergoes ring opening to become a chain dimer of lactic acid or lactic acid that can decompose the polylactic acid or copolymer thereof. Thus, these biodegradable materials decompose rapidly and exhibit a poor storage stability or thermal stability. Further, the content of residual lactide varies widely from lot to lot. Therefore, these biodegradable materials have varied biodegradability and thus can hardly be reproduced.

SUMMARY OF THE INVENTION

It is therefore an object of the present invention to provide a biodegradable material having excellent organic compatibility, formability, mechanical properties, biodegradability and storage stability which can be used as bone substitute material, material for osteosynthesis, bone filling material, dental material, material having controlled release of chemical, material having controlled release of physiologically active compound or the like and a process for the preparation thereof.

The foregoing object of the present invention will become more apparent from the following detailed description and examples.

The inventors have found that the use of a lactic acid-based polymer having a specific composition consisting of structural units derived from lactic acid components and polyester structural units derived from dicarboxylic acid components and diol components and having a reduced content of residual lactide makes it possible to control the biodegradation rate, inhibiting inflammatory reaction at the embedded site, and provide a good storage stability. The inventors have also found that the dissolution of the foregoing lactic acid-based polymer in a solvent, followed by the removal of the solvent, the polymer makes it possible to produce a porous material at which the induction and regeneration of fibrous tissue or osseous tissue can be accelerated. The inventors have further found that the completing of the foregoing lactic acid-based polymer with a calcium phosphate-based compound and/or a water-soluble polymer such as polyethylene glycol and poly(N-vinylpyrrolidone) in various proportions makes it possible to enhance the controllability of biodegradation of the biodegradable material in the living body and the dissolution and separation of the water-soluble polymer from the composite makes it possible to produce a porous composite at which the induction and regeneration of fibrous tissue and osseous tissue can be accelerated. Thus, the present invention has been worked out.

The present invention concerns a biodegradable material, comprising as essential components a lactic acid-based polymer (A) consisting of structural units (a) derived from lactic acid components and polyester structural units (b) derived from dicarboxylic acid components and diol components, the weight ratio of (a)/(b) being from 98/2 to 20/80, and a calcium phosphate-based compound (B), wherein the weight ratio of (A)/(B) is from 99/1 to 30/70.

The present invention also concerns a biodegradable material, comprising as essential components a lactic acid-based polymer (A) consisting of structural units (a) derived from lactic acid components and polyester structural units (b) derived from dicarboxylic acid components and diol components, the weight ratio of (a)/(b) being from 98/2 to 20/80, and a polyethylene glycol and/or poly(N-vinylpyrrolidone) (C), wherein the weight ratio of (A)/(C) is from 95/5 to 50/50.

The present invention further concerns a biodegradable material, comprising as essential components a lactic acid-based polymer (A) consisting of structural units (a) derived from lactic acid components and polyester structural units (b) derived from dicarboxylic acid components and diol components, the weight ratio of (a)/(b) being from 98/2 to 20/80, a calcium phosphate-based compound (B), and a polyethylene glycol and/or poly(N-vinylpyrrolidone) (C), wherein the weight ratio of (A)/(B+C) is from 99/1 to 50/50.

The present invention further concerns a process for the preparation of a biodegradable material, which comprises dissolving a lactic acid-based polymer (A) consisting of structural units (a) derived from lactic acid components and polyester structural units (b) derived from dicarboxylic acid components and diol components, the weight ratio of (a)/(b) being from 98/2 to 20/80, in a solvent, removing the solvent from the solution or dispersion, and then forming the material.

The present invention further concerns a process for the preparation of a biodegradable material, which comprises dissolving a lactic acid-based polymer (A) consisting of structural units (a) derived from lactic acid components and polyester structural units (b) derived from dicarboxylic acid components and diol components, the weight ratio of (a)/(b) being from 98/2 to 20/80, in a solvent, dispersing a calcium phosphate-based compound (B) in the solution in such an amount that the weight ratio (A)/(B) is from 99/1 to 30/70, removing the solvent from the solution or dispersion, and then forming the material.

The present invention further concerns a process for the preparation of a biodegradable material, which comprises dissolving a lactic acid-based polymer (A) consisting of structural units (a) derived from lactic acid components and polyester structural units (b) derived from dicarboxylic acid components and diol components, the weight ratio of (a)/(b) being from 98/2 to 20/80, in a solvent, dispersing or dissolving a polyethylene glycol and/or poly(N-vinylpyrrolidone) (C) in the solution in such an amount that the weight ratio (A)/(C) is from 95/5 to 50/50, removing the solvent from the solution or dispersion, and then forming the material.

The present invention further concerns a process for the preparation of a biodegradable material, which comprises dissolving a lactic acid-based polymer (A) consisting of structural units (a) derived from lactic acid components and polyester structural units (b) derived from dicarboxylic acid components and diol components, the weight ratio of (a)/(b) being from 98/2 to 20/80, in a solvent, dispersing or dissolving a calcium phosphate-based compound (B) and a polyethylene glycol and/or poly(N-vinylpyrrolidone) (C) in the solution in such an amount that the weight ratio (A)/(B+C) is from 99/1 to 50/50, removing the solvent from the solution or dispersion, and then forming the material.

The present invention concerns a process for the preparation of a biodegradable material, which comprises kneading a lactic acid-based polymer (A) consisting of structural units (a) derived from lactic acid components and polyester structural units (b) derived from dicarboxylic acid components and diol components, the weight ratio of (a)/(b) being from 98/2 to 20/80, and a calcium phosphate-based compound (B) at a temperature of not lower than the melting point of said lactic acid-based polymer (A) in such an amount that the weight ratio (A)/(B) is from 99/1 to 30/70.

The present invention further concerns a process for the preparation of a biodegradable material, which comprises kneading a lactic acid-based polymer (A) consisting of structural units (a) derived from lactic acid components and polyester structural units (b) derived from dicarboxylic acid components and diol components, the weight ratio of (a)/(b) being from 98/2 to 20/80, and a polyethylene glycol and/or poly(N-vinylpyrrolidone) (C) at a temperature of not lower than the melting point of said lactic acid-based polymer (A) in such an amount that the weight ratio (A)/(C) is from 95/5 to 50/50.

The present invention further concerns a process for the preparation of a biodegradable material, which comprises kneading a lactic acid-based polymer (A) consisting of structural units (a) derived from lactic acid components and polyester structural units (b) derived from dicarboxylic acid components and diol components, the weight ratio of (a)/(b) being from 98/2 to 20/80, a calcium phosphate-based compound (B) and a polyethylene glycol and/or poly(N-vinylpyrrolidone) (C) at a temperature of not lower than the melting point of said lactic acid-based polymer (A) in such an amount that the weight ratio (A)/(B+C) is from 99/1 to 50/50.

DETAILED DESCRIPTION OF THE INVENTION

The lactic acid-based polymer, calcium phosphate-based compound, polyethylene glycol and poly(N-vinylpyrrolidone) to be incorporated in the biodegradable material of the present invention will be further described hereinafter.

The lactic acid-based polymer (A) consisting of structural units (a) derived from lactic acid components and polyester structural units (b) derived from dicarboxylic acid components and diol components, the weight ratio of (a)/(b) being from 98/2 to 20/80, has a biodegradability, a high flexural strength and elastic modulus and an excellent moldability.

The process for the preparation of the lactic acid-based polymer (A) is not specifically limited. In practice, however, a process may be employed which comprises allowing a polyester prepared from dicarboxylic acid components and diol components to undergo ring-opening polymerization and ester exchange reaction with a lactide as a cyclic dimer of lactic acid in the presence of a ring-opening polymerization catalyst. Alternatively, a process may be employed which comprises dehydrating and deglycolating lactic acid, dicarboxylic acid components and diol components in the presence of a catalyst and a solvent so that they undergo polycondensation as disclosed in JP-A-7-172425. Further, a process may be employed which comprises allowing a polyester derived from dicarboxylic acid components and diol components and a polylactic acid to undergo ester exchange reaction.

The polyester consisting of dicarboxylic acid components and diol components to be used in the preparation of the foregoing lactic acid-based polymer has an effect of enhancing the flexibility, particularly folding endurance or impact resistance, of the lactic acid-based polymer. The more the polyester content is, the lower is the acidity of the lactic acid-based polymer during biodegradation and the more can be inhibited the inflammatory reaction at the embedded site due to biodegradation.

The process for the preparation of the foregoing polyester is not specifically limited. In practice, however, any known methods may be employed. For example, a process may be employed which comprises dehydrating and deglycolating dicarboxylic acid components and diol components in the presence of an esterification catalyst so that they undergo polycondensation. Alternatively, a process may be employed which comprises allowing dicarboxylic acid components and diol components to undergo dehydration/deglycolation condensation or ester exchange reaction in the presence of a catalyst and a solvent.

The foregoing polylactic acid may be prepared by a process which comprises the ring-opening polymerization of a lactide in the presence of a ring-opening polymerization catalyst or a process which comprises the polycondensation of a lactic acid in the presence or absence of a solvent as disclosed in JP-A-6-172502.

Examples of the lactic acid component as a constituent of the lactic acid-based polymer to be used in the present invention include lactic acid, and lactide. Lactic acid has optical isomers and is in the form of L-lactic acid or D-lactic acid. Lactide has optical isomers, i.e., D-lactide, L-lactide and meso-lactide. The combination of these optical isomers can realize desirable polymer properties.

The biodegradable material of the present invention preferably has a lactic acid component having a high optical activity to realize a high heat resistance. In some detail, the lactic acid component preferably contains L-form or D-form in an amount of not less than 70% by weight based on the weight of the total lactic acid. In order to obtain an even better heat resistance, the lactic acid component preferably contains L-form or D-form in an amount of not less than 85% by weight based on the weight of the total lactic acid.

If a lactide is used, L-lactide or D-lactide is preferably incorporated in an amount of not less than 70% by weight based on the weight of the total lactide. In order to obtain an even better heat resistance, L-lactide or D-lactide is preferably incorporated in an amount of not less than 85% by weight based on the weight of the total lactide.

The weight-average molecular weight of the lactic acid-based polymer to be used in the present invention depends on the required mechanical properties and biodegradation rate of the biodegradable material, kneadability, if kneaded, etc. In general, it is from 10,000 to 400,000. If high mechanical properties are required, the weight-average molecular weight of the lactic acid-based polymer is preferably not less than 20,000. If a composition having a high content of calcium phosphate-based compound or water-soluble polymer based on the lactic acid-based polymer is melted and kneaded to prepare the desired biodegradable material, the weight-average molecular weight of the lactic acid-based polymer during kneading is preferably from 40,000 to 350,000, more preferably from 40,000 to 300,000.

If the weight-average molecular weight of the lactic acid-based polymer falls below 10,000, the resulting lactic acid-based polymer has insufficient mechanical properties. On the contrary, if the weight-average molecular weight of the lactic acid-based polymer exceeds 400,000, the resulting lactic acid-based polymer has a poor productivity and moldability. As the polyester from which the lactic acid-based polymer is prepared there may be preferably used a polyester which normally stays solid because the resulting lactic acid-based polymer tends to undergo less bleedout. The content of residual lactide in the lactic acid-based polymer is not more than 0.5% by weight, preferably not more than 0.2% by weight.

The content of the polyester corresponding to the polyester structural units (b) derived from dicarboxylic acid components and diol components in the lactic acid-based polymer (A) of the present invention is preferably from 2% by weight to 80% by weight based on the lactic acid components, more preferably from 4% by weight to 60% by weight. If the polyester content falls below 2% by weight, the resulting biodegradable material exhibits an insufficient flexibility, making it impossible to realize good control over biodegradability and inhibition of inflammatory reaction. On the contrary, if the polyester content exceeds 80% by weight, the desired mechanical properties cannot be obtained.

As the polymerization catalyst to be used in the preparation of the lactic acid-based polymer of the present invention there may be used a known polymerization catalyst such as ring-opening polymerization catalyst, esterification catalyst and ester exchange catalyst. Examples of such a polymerization catalyst include metals such as tin, zinc, lead, titanium, bismuth, zirconium, germanium and cobalt, and compounds thereof. Preferred examples of metallic compounds include metallic organic compounds, metal carbonates, and metal halides.

Specific examples of these metallic compounds include tin octanoate, tin chloride, zinc chloride, zinc acetate, lead oxide, lead carbonate, titanium chloride, diacetoacetoxyoxy titanium, tetraethoxy titanium, tetrapropoxy titanium, tetrabutoxy titanium, germanium oxide, and zirconium oxide. The amount of such a metallic compound to be incorporated is preferably from 0.001 to 2 parts by weight, more preferably from 0.002 to 0.5 parts by weight based on 100 parts by weight of the reaction components from the standpoint of reaction rate, colorability, etc.

As the esterification catalyst to be used in the preparation of the polyester consisting of dicarboxylic acid components and diol components there may be used one similar to the foregoing catalyst. The esterification catalyst is preferably added to the reaction system at the beginning of the esterification reaction or shortly before the deglycolation reaction.

The reaction temperature at which the lactic acid-based polymer of the present invention is produced depends on the kind, amount, combination, etc. of lactic acid component, dicarboxylic acid component and diol component. In general, it is from 125° C. to 250° C., preferably from 140° C. to 230° C., more preferably from 150° C. to 200° C. The dicarboxylic acid component and diol component as constituents of the polyester to be used in the present invention will be further described hereinafter.

The dicarboxylic acid component to be used herein is not specifically limited but is preferably an aliphatic dicarboxylic acid component from the standpoint of biodegradability. Specific examples of such an aliphatic dicarboxylic acid component include malonic acid, succinic acid, glutaric acid, adipic acid, 2-methyladipic acid, pimelic acid, cork acid, azelaic acid, sebacic acid, nonanedicarboxylic acid, decanedicarboxylic acid, undecanedicarboxylic acid, dodecanedicarboxylic acid, maleic anhydride, fumaric acid, citraconic acid, diglycolic acid, cyclohexa-3,5-diene-1,2-carboxylic acid, maleic acid, citric acid, trans-hexahydroterephthalic acid, cis-hexahydroterephthalic acid, dimeric acid, and mixture thereof. In particular, the use of a $C_{4-20}$ aliphatic dicarboxylic acid component provides a biodegradable material with an excellent flexibility.

The diol component to be used herein is not specifically limited but is preferably one free of aromatic ring from the standpoint of biodegradability. Specific examples of such a diol component include ethylene glycol, propylene glycol, trimethylene glycol, butane-1,2-diol, butane-1,3-diol, butane-1,4-diol, butane-2,3-diol, 2,2-dimethylpropane-1,3-diol, cis-2-butene-1,4-diol, trans-2-butene-1,4-diol, tetramethylene glycol, pentamethylene glycol, hexamethylene glycol, heptamethylene glycol, octamethylene glycol, nonamethylene glycol, decamethylene glycol, undecamethylene glycol, dodecamethylene glycol, tridecamethylene glycol, eicosamethylene glycol, trans-1,4-cyclohexanedimethanol, 2,2,4-trimethylpentane-1,3-diol, hydrogenated bisphenol A, p-xylylene glycol, diethylene glycol, triethylene glycol, dipropylene glycol, tripropylene glycol, and mixture thereof.

Further, the use of a polyoxyalkylene containing many ether-bonded oxygen atoms provides a biodegradable material with an excellent flexibility. Examples of such a polyoxyalkylene include polyethylene glycol, polypropylene glycol, polybutylene glycol, polypentanediol, polytetramethylene glycol, and block copolymer of polyethylene glycol and polypropylene glycol.

In order to enhance the thermal stability or the storage stability of the biodegradable material during melt kneading or melt molding, it is effective to reduce the content of an acid component such as residual lactide, lactic acid and oligomer thereof in the lactic acid-based polymer (A). The reduction of the acid content in the lactic acid-based polymer (A) can be accomplished by means of a devolatilizing apparatus such as devolatilizing tank, film evaporator and vented extruder provided after the lactic acid-based polymer producing step. Alternatively, it can be accomplished by a solvent separating method. Further, the biodegradable material may be soaked or dispersed in a solvent such as alcohol, ketone and hydrocarbon rather than dissolved in the solvent, followed by the extraction and removal of the acid component.

The deactivation of the polymerization catalyst which has been used in the polymerization reaction for the preparation of the lactic acid-based polymer makes it possible to reduce the content of an acid component such as lactide, lactic acid and oligomer thereof in the lactic acid-based polymer. The deactivation of the polymerization catalyst can be accomplished by adding a catalyst deactivator to the reaction system or allowing the reaction system to come in contact with such a catalyst deactivator at the end of or during the lactic acid-based polymer production step so that the deactivator reacts with the catalyst in the polymer. Particularly preferred examples of the polymerization catalyst deactivator include acid phosphate, and chelating agent.

Examples of the chelating agent to be used as the polymerization catalyst deactivator include organic chelating agents and inorganic chelating agents. Organic chelating agents exhibit a low hygroscopicity and an excellent thermal stability. The organic chelating agents employable herein are not specifically limited. Examples of these organic chelating agents include amino acids, phenols, hydroxycarboxylic acids, diketones, amines, oximes, phenanthrolines, pyridine compounds, dithio compounds, phenols including coordinated atom N, carboxylic acids including coordinated atom N, diazo compounds, thiols, and porphyrins.

Specific examples of amino acids include glycine, leucine, alanine, serine, α-aminobutyric acid, acetylaminoacetic acid, glycylglycine, and glutamic acid. Specific examples of phenols include alizarin, t-butylcatechol, 4-isopropyltropone, chromotropic acid, tiron, oxine, and propyl gallate. Specific examples of hydroxycarboxylic acids include tartaric acid, oxalic acid, citric acid, monooctyl citrate, dibenzoyl-D-tartaric acid, and diparatoluoil-D-tartaric acid. Specific examples of diketones include acetylacetone, hexafluoroacetylacetone, benzoylacetone, ternoyltrifluoroacetone, and trifluoroacetylacetone. Specific examples of amines include ethylenediamine, diethylenetriamine, 1,2,3-triaminopropane, thiodiethylamine, triethylenetetramine, triethanolamine, tetraethylenepentamine, and pentaethylenehexamine. Specific examples of oxime include dimethylglyoxime, α,α-furyldioxime, and salithylaldoxime. Specific examples of phenanethrolines include neocuproine, and 1,10-phenanethroline. Specific examples of pyridine compounds include 2,2-bipyridine, and 2,2',2"-terpyridyl. Specific examples of dithio compounds include xanthogenic acid, diethyldithiocarbamic acid, and toluene-3,4-dithiol. Specific examples of phenols including coordinated atom N include o-aminophenol, oxine, nitroso R salt, 2-nitroso-5-dimethylaminophenol, 1-nitroso-2-naphthol, and 8-selenoquinoline. Specific examples of carboxylic acids including coordinated atom N include quinaldic acid, nitrilotriacetic acid, ethylenediaminediacetic acid, hydroxyethyl-ethylenediaminetriacetic acid, ethylenediamine tetraacetic acid, trans-cyclohexanediaminetetraacetic acid, diethylen-etriaminepentaacetic acid, triethylenetetramine hexaacetic acid, anilinediacetic acid, 2-sulfoanilinediacetic acid, 3-sulfoanilinediacetic acid, 4-sulfoanilinediacetic acid, 2-aminobenzoic acid-N,N-diacetic acid, 3-aminobenzoic acid-N,N-diacetic acid, 4-aminobenzoic acid-N,N-diacetic acid, methylaminediacetic acid, β-alanine-N,N-diacetic acid, β-aminoethylsulfonic acid-N,N-diacetic acid, and β-aminoethylphosphonic acid-N,N-diacetic acid. Specific examples of diazo compounds include diphenylcarbazone, magneson, dithizone, eriochrome black T, 4-(2-thiazolylazo) resorcine, and 1-(2-pyridylazo)-2-naphthol. Specific examples of thiols include thiooxine, thionalide, 1,1,1-trifluoro-4-(2-chenyl)-4-mercapto-3-butene-2-one, and 3-mercapto-p-cresol. Specific examples of porphyrines include tetraphenylporphyrin, and tetrakis(4-N-methylpyridyl) porphyrin. Other examples of organic chelating agents include cupferron, murexide, polyethyleneimine, polymethylacryloylacetone, polyacrylic acid, and mixture thereof.

Among these organic chelating agents, those which efficiently coordinate with metallic ions in the catalyst contained in the lactic acid-based polyester to inhibit the scission of polymer terminal are carboxylic acids including coordinated atom N such as nitrilotriacetic acid, ethylene diaminediacetic acid, tetraethylenepentamine, hydroxyethyl ethylenediaminetriacetic acid, ethylenediaminetetraacetic acid, trans-cyclohexanediaminetetraacetic acid, diethylene triaminepentaacetic acid and triethylenetetraminehexaacetic acid, and hydroxycarboxylic acids such as tartaric acid, dibenzoyl-D-tartaric acid, diparatoluoil-D-tartaric acid, citric acid and monooctyl citrate. In particular, the foregoing carboxylic acids including coordinated atom N exhibit an excellent thermal stability or storage stability. The foregoing hydroxycarboxylic acids are characterized by a low colorability.

Inorganic chelating agents exhibit a high hygroscopicity and thus lose its effect when moistened. Therefore, these inorganic chelating agents should be handled with caution. Specific examples of inorganic chelating agents employable herein include phosphoric acids such as phosphoric acid, phosphorous acid, pyrophosphoric acid and polyphosphoric acid.

Acid phosphates exert an effect of complexing with metallic ions in the catalyst contained in the lactic acid-based polyester to eliminate the catalytic activity and hence inhibit the scission of polymer chain. Examples of acid phosphates include acid phosphate, ester phosphonate, alkylphosphonic acid, and mixture thereof. The general formula of such an acid phosphate will be given below.

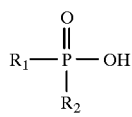

wherein $R_1$ represents an alkyl group or an alkoxyl group; and $R_2$ represents an alkyl group, an alkoxyl group or a hydroxyl group.

Specific examples of thee acid phosphates include monomethyl phosphate, dimethyl phosphate, monoethyl phosphate, diethyl phosphate, monopropyl phosphate, dipropyl phosphate, monoisopropyl phosphate, diisopropyl phosphate, monobutyl phosphate, dibutyl phosphate, monopentyl phosphate, dipentyl phosphate, monohexyl phosphate, dihexyl phosphate, monooctyl phosphate, dioctyl phosphate, mono-2-ethylhexyl phosphate, di-2-ethylhexyl phosphate, monodecyl phosphate, didecyl phosphate, monoisodecyl phosphate, diisodecyl phosphate, monoundecyl phosphate, diundecyl phosphate, monododecyl phosphate, didodecyl phosphate, monotetradecyl phosphate, ditetradecyl phosphate, monohexadecyl phosphate, dihexadecyl phosphate, monooctadecyl phosphate, dioctadecyl phosphate, monophenyl phosphate, diphenyl phosphate, monobenzyl phosphate, and dibenzyl phosphate. Specific examples of ester phosphonate include monomethyl phosphonate, monoethyl phosphonate, monopropyl phosphonate, monoisopropyl phosphonate, monobutyl phosphonate, monopentyl phosphonate, monohexyl phosphonate, monooctyl phosphonate, monoethylhexyl phosphonate, monodecyl phosphonate, monoisodecyl phosphonate, monoundecyl phosphonate, monododecyl phosphonate, monotetradecyl phosphonate, monohexadecyl phosphonate, monooctadecyl phosphonate, monophenyl phosphonate, and monobenzyl phosphonate. Specific examples of alkylphosphonic acid include monomethylphosphonic acid, dimethylphosphonic acid, monoethylphosphonic acid, diethylphosphonic acid, monopropylphosphonic acid, dipropylphosphonic acid, monoisopropylphosphonic acid, diisopropylphosphonic acid, monobutylphosphonic acid, dibutylphbsphonic acid, monopentylphosphonic acid, dipentylphosphonic acid, monohexylphosphonic acid, dihexylphosphonic acid, isooctylphosphonic acid, dioctylphoshonic acid, monoethylhexylphosphonic acid, diethylhexylphosphonic acid, monodecylphosphonic acid, didecylphosphonic acid, monoisodecylphosphonic acid, diisodecylphosphonic acid, monoundecylphosphonic acid, diundecylphosphonic acid, monododecylphosphonic acid, didodecylphosphonic acid, monotetradecylphosphonic acid, ditetradecylphosphonic acid, monohexadecylphosphonic acid, dihexadecylphosphonic acid, monooctadecylphosphonic acid, dioctadecylphosphonic acid, monophenylphosphonic acid, diphenylphosphonic acid, monobenzylphosphonic acid, dibenzylphosphonic acid, and mixture thereof.

The acid phosphate component exhibits a good solubility in an organic solvent and hence an excellent handling and reactivity with the lactic acid-based polyester. In particular, the acid phosphate exerts a great effect of deactivating the catalyst.

The amount of the chelating agent and/or acid phosphate to be added to deactivate the polymerization catalyst depends on the kind thereof and the kind and amount of the catalyst contained in the lactic acid-based polyester. In practice, however, it is preferably from 0.001 to 5 parts by weight based on 100 parts by weight of the lactic acid-based polyester. Any of these chelating agents and acid phosphates can minimize the scission of polymer chain. These organic chelating agents, inorganic chelating agents and acid phosphates may be used in admixture.

However, if these chelating agents or acid phosphates are added in excess, the lactic acid-based polyester chain is cut during storage to lower the molecular weight and viscosity thereof, possibly making it impossible to obtain the desired properties of the present invention. It is thus necessary to use an optimum amount of chelating agents.

The reduction of the content of the acid component such as lactide, lactic acid and oligomer thereof in the lactic acid-based polymer after the deactivation of the polymerization catalyst can be accomplished by means of a devolatilizing apparatus such as devolatilizing tank, film evaporator and vented extruder provided after the polymerization catalyst deactivation step. Alternatively, it can be accomplished by dissolving the lactic acid-based polymer in a good solvent, and then treating the solution in a poor solvent so that the acid component is precipitated therein. Further, the lactic acid-based polymer may be soaked or dispersed in a solvent such as alcohol, ketone and hydrocarbon rather than dissolved in the solvent, followed by the extraction and removal of the acid component.

In order to enhance the safety of the biodegradable material in the living body, it is effective to remove the catalyst from the lactic acid-based polymer. The removal of the catalyst can be accomplished by any known method. For example, the lactic acid-based polymer may be dissolved in an organic solvent, and then allowed to come in contact with an acidic substance and water to allow the separation of an organic phase containing the catalyst as disclosed in JP-A-8-34844 and JP-A-8-109250.

The calcium phosphate-based compound (B) to be complexed with the lactic acid-based polymer of the present invention exerts an effect of enhancing the elastic modulus of the lactic acid-based polymer as well as neutralizing an organic acid produced by the biodegradation process and hence inhibiting the decomposition of the biodegradable material with such an organic acid to inhibit the inflammatory reaction, which is one of the prior art problems. The calcium phosphate-based compound is a constituent of bone which is bioactive and exerts an effect of accelerating the induction or regeneration of osseous tissue.

The term "calcium phosphate-based compound" as used herein is meant to indicate a compound comprising a moiety derived from phosphoric acid and calcium atoms in a total amount of not less than 50%. Specific examples of such a calcium phosphate-based compound include tricalcium phosphate, hydroxyapatite, carbonate apatite, fluorinated hydroxyapatite, and magnesium-containing hydroxyapatite. Such a calcium phosphate-based compound may have any crystalline structure or may be amorphous.

The powdered calcium phosphate-based compound to be used in the present invention indicates an aggregate of powdery mass of calcium phosphate-based compound having a maximum diameter of not more than 5 mm. The shape of mass is not specifically limited. In some detail, the mass may be spherical, porous or amorphous. The size of the mass ranges from that of finely divided powder to that of granule. The process for the preparation of tricalcium phosphate to be used in the present invention is not specifically limited. In practice, however, dry process, hydrothermal process or wet process may be employed. The product thus obtained may be subjected to heat treatment. The process for the preparation of hydroxyapatite, too, is not specifically limited. In practice, however, dry process, hydrothermal process, wet process or alkoxide process may be employed. The product thus obtained may be subjected to heat treatment.

The composite material of the lactic acid-based polymer of the present invention with the calcium phosphate-based compound of the present invention differs in requirements such as elastic modulus, biodegradation rate and absorption rate of composite material and regeneration rate of fibrous tissue or osseous tissue from purpose to purpose. Thus, the weight ratio of the lactic acid-based polymer to the calcium phosphate compound cannot be absolutely defined. In general, however, it is from 99/1 to 30/70, preferably from 98/2 to 55/45, more preferably from 98/2 to 60/40. If the content of the calcium phosphate-based compound based on the lactic acid-based polymer exceeds 70 parts by weight, the mixture cannot be sufficiently melt-kneaded, resulting in the production of a composite having a poor moldability. The biodegradable material thus obtained tends to become brittle.

The preparation of the biodegradable material of the present invention can be accomplished by a process which comprises dissolving the lactic acid-based polymer (A) in a solvent, removing the solvent from the solution, and then forming the material. The removal of the solvent renders the polymer porous. The porous material thus obtained exhibits a desirable compatibility and biodegradability in the living body.

The water-soluble polymer such as polyethylene glycol and poly(N-vinylpyrrolidone) in the polyethylene glycol and/or poly(N-vinylpyrrolidone) (C) to be used in the present invention can be relatively easily dissolved in the living body when used in the form of composite with the lactic acid-based polymer. As a result, the composite is rendered porous, making it easy to diffuse an organic acid produced at the biodegradation process and hence making it possible to inhibit undesirable inflammatory reaction and accelerate the induction and regeneration of fibrous tissue or osseous tissue.

Therefore, water-soluble polymers other than polyethylene glycol and/or poly(N-vinylpyrrolidone) can be used in the present invention.

Polyethylene glycols occur with a molecular weight of from 200 to 2,000,000 and differ in handling and solubility in the living body depending on the molecular weight. In some detail, those having a molecular weight of from 200 to 600 occur in the form of viscous liquid. Those having a molecular weight of from 1,000 to 6,000 occur in the form of solid at room temperature. Those having a molecular weight of not less than 4,000 occur in the form of hard wax. These polyethylene glycols have an excellent thermal stability and can be melt-kneaded with the lactic acid-based polymer (A) at a temperature of not higher than the melting point of the lactic acid-based polymer (A). Even when the polyethylene glycol and the lactic acid-based polymer (A) are not completely uniformly dissolved and mixed, it suffices if the two components are kneaded in fine dispersion.

Poly(N-vinylpyrrolidone) has a molecular weight of from 10,000 to 700,000 and is in the form of white powder. It doesn't undergo thermal decomposition even at a temperature high as not lower than 150° C. In the case where the poly(N-vinylpyrrolidone) is melt-kneaded with the lactic acid-based polymer (A) to prepare a biodegradable material, if the kneading is effected at a temperature of not lower than 150° C., the poly(N-vinylpyrrolidone) is insolubilized, deteriorating the compatibility of the biodegradable material of the present invention with the living body. Therefore, if the lactic acid-based polymer (A) and the poly(N-vinyl pyrrolidone) are melt-kneaded free from solvent, the kneading is preferably effected at a temperature of from not lower than the melting point of the lactic acid-based polymer (A) to not higher than 150° C. It suffices if the poly(N-vinyl pyrrolidone) and the lactic acid-based polymer (A) are kneaded in fine dispersion.

The biodegradable material of the present invention may comprise as water-soluble substances saccharides such as cellulose polymer, oligosaccharide and grape sugar, physiologically acceptable salts and esters of polyethylene glycol and saturated aliphatic acid incorporated therein in admixture besides polyethylene glycol and poly(N-vinylpyrrolidone) in such an amount that the desired mechanical properties cannot be impaired.

The composite material of the lactic acid-based polymer (A) with the water-soluble polymer of the present invention differs in requirements such as elastic modulus, biodegradation rate and absorption rate of composite material and induction rate and regeneration rate of fibrous tissue or osseous tissue from purpose to purpose. Thus, the weight ratio of the lactic acid-based polymer to the water-soluble polymer cannot be absolutely defined. In general, however, it is from 95/5 to 50/50, preferably from 90/10 to 50/50, more preferably from 90/10 to 60/40.

If the content of the water soluble polymer such as polyethylene glycol and/or poly(N-vinylpyrrolidone) (C) based on the lactic acid-based polymer exceeds 50% by weight, the melt-kneadability of the mixture is deteriorated, making it difficult to obtain a porous material suitable for the regeneration of tissues.

In the biodegradable material comprising the lactic acid-based polymer (A) of the present invention, the combined use of the calcium phosphate-based compound (B) and the polyethylene glycol and/or poly(N-vinylpyrrolidone) (C) provides a composite material having a raised degree of freedom of control over elastic modulus, biodegradation rate, and induction and regeneration rate of fibrous tissue or osseous tissue as compared with the single use of these components.

In the biodegradable material of the present invention, the preferred total of the content of the lactic acid-based polymer (A), calcium phosphate-based compound (B) and polyethylene glycol and/or poly(N-vinylpyrrolidone) (C), i.e., the weight ratio (A)/(B+C) is normally from 99/1 to 50/50, preferably from 98/2 to 55/45, more preferably from 95/5 to 60/40.

If the total weight of the calcium phosphate-based compound (B) and the polyethylene glycol and/or poly(N-vinylpyrrolidone) (C) based on the weight of the lactic acid-based polymer (A) exceeds the above defined range, the melt-kneadability of the mixture is deteriorated, resulting in the production of a brittle composite material having a poor moldability. Thus, the desirable porous material cannot be obtained.

The biodegradable material of the present invention may comprise physiologically active compounds and chemicals incorporated therein. The biodegradable material of the present invention may further comprise a polylactic acid, a polyglycolic acid or copolymer thereof incorporated therein in combination in such an amount that the desired mechanical properties cannot be impaired.

The biodegradable material of the present invention is capable of gradually releasing chemicals as well as has a high affinity for tissues in the living body. Thus, the biodegradable material of the present invention undergoes biodegradation and doesn't need to be taken out from the living body. Therefore, the biodegradable material of the present invention can be used as a gradually-releasable chemical. Further, since the biodegradable material of the present invention has an excellent flexibility, it can be used as a chemical-filled material for soft tissue.

In addition to high affinity for tissue and capability of gradually releasing chemicals, the biodegradable material of the present invention exhibits excellent flexural strength and elastic modulus. Thus, the biodegradable material of the present invention can be used as an artificial bone capable of gradually releasing chemicals such as antibiotic and carcinostatic.

The process for the preparation of the biodegradable material of the present invention will be described hereinafter. The preparation of the porous material made of the lactic acid-based polymer (A) can be accomplished by a process which comprises dissolving the lactic acid-based polymer (A) in a solvent such as dioxane, chloroform, dichloroethane and THF, drying the solution under normal or reduced pressure or freeze-drying the solution, and then forming the material at reduced or raised pressure to obtain the desired formed product. The removal of the solvent from the polymer renders the resulting biodegradable material porous. Thus, a desirable biodegradable material can be obtained.

The preparation of the porous composite material of the lactic acid-based polymer (A) with the calcium phosphate-based compound (B) can be accomplished by a process which comprises dissolving the lactic acid-based polymer (A) in a solvent such as dioxane, chloroform, dichloroethane and THF, dispersing the calcium phosphate-based compound (B) in the solution, drying the dispersion under normal or reduced pressure or freeze-drying the dispersion, and then forming the material under reduced or raised pressure to obtain a desired formed product. The drying under reduced pressure is preferably effected by means of a thin film process dryer so that the polymer can be rendered porous deep inside.

The preparation of the porous composite material of the lactic acid-based polymer (A) with the polyethylene glycol and/or poly(N-vinylpyrrolidone) (C) can be accomplished by a process which comprises dissolving or finely dispersing these components in a solvent such as dioxane, chloroform, dichloroethane and THF, dispersing or dissolving a water-soluble polymer in the solution or dispersion, drying the dispersion under normal or reduced pressure or freeze-drying the dispersion, and then forming the material under reduced or raised pressure to obtain a desired formed product.

The preparation of the porous composite material of the lactic acid-based polymer (A) with the calcium phosphate-based compound (B) and the polyethylene glycol and/or poly(N-vinylpyrrolidone) (C) can be accomplished by a process which comprises dissolving the lactic acid-based polymer in a solvent such as dioxane, chloroform, dichloroethane and THF, dissolving or dispersing the calcium phosphate-based compound and the polyethylene glycol and/or poly(N-vinylpyrrolidone), drying the solution or dispersion under normal or reduced pressure or freeze-drying the dispersion, and then forming the material under reduced or raised pressure to obtain a desired formed product.

The preparation of the melt composite material of the lactic acid-based polymer (A) with the calcium phosphate-based compound (B) can be accomplished by a process which comprises melting the lactic acid-based polymer, dispersing the calcium phosphate-based compound in the molten lactic acid-based polymer while removing volatile matter, pelletizing the dispersion through an extruder, and then forming the pellets by means of a forming machine to obtain a desired formed product.

The preparation of the melt composite material of the lactic acid-based polymer (A) with the polyethylene glycol and/or poly(N-vinylpyrrolidone) (C) can be accomplished by a process which comprises kneading these components at a temperature of not lower than the melting point of the lactic acid-based polymer (A) while removing volatile matter, and then forming the material. The temperature at which the kneading with poly(N-vinylpyrrolidone) is effected is preferably from not lower than the melting point of the lactic acid-based polymer (A) to not higher than 150° C. The components (A) and (C) don't need to be thoroughly melted and dissolved. It suffices if they are uniformly and finely dispersed in each other. The dispersion may be pelletized through an extruder, and then formed by means of a forming machine to obtain a desired formed product.

The temperature at which the kneading with polyethylene glycol is effected is not specifically limited. In practice, however, the kneading is preferably effected at a temperature of not lower than the melting point of the lactic acid-based polymer (A). The biodegradable material comprising a melt dispersion of the lactic acid-based polymer (A) with the calcium phosphate-based compound (B) and the polyethylene glycol and/or poly(N-vinylpyrrolidone) (C) of the present invention can be obtained by a process similar to the foregoing process. Though not specifically limited in the order of addition, the components (A) and (C) are normally kneaded at a temperature of from not lower than the melting point of the lactic acid-based polymer (A) to not higher than 150° C. To the mixture is then added the component (B). These components are then kneaded while removing volatile matter. The material is pelletized through an extruder, and then formed by a forming machine to obtain a desired formed product.

The apparatus for the preparation of the biodegradable material of the present invention from the lactic acid-based polymer (A) and the calcium phosphate-based compound (B) and/or poly(N-vinylpyrrolidone) (C) will be further described hereinafter.

The apparatus for the preparation of the biodegradable material of the present invention is not specifically limited.

In practice, however, the complexing of the lactic acid-based polymer with the calcium phosphate-based compound and/or the polyethylene glycol and/or poly(N-vinylpyrrolidone) can be accomplished by means of an extruder, reactor, kneader, and roll, singly or in combination.

As the extruder there may be used a single-screw extruder or twin-screw extruder. A twin-screw extruder is preferably used from the standpoint of kneading conditions. The extruder is preferably vented to remove the residual volatile matter under reduced pressure subsequently after kneading. As the reactor there may be used an ordinary reactor. In practice, however, since the materials to be kneaded exhibit a high viscosity and thus undergoes a high stirring shear stress that causes the generation of heat resulting in the drop of molecular weight or coloring, a static mixer which causes a low shearing stress and provides uniform mixing is preferably used.

Referring to specific kneading conditions, the kneading temperature depends on the melting point of the lactic acid-based polymer (A) used. In practice, however, it is normally from 50° C. to 250° C., preferably from 60° C. to 200° C. However, it is necessary that the kneading with poly(N-vinylpyrrolidone) be effected at a temperature of not higher than 150° C. The kneading is preferably effected while removing the residual volatile matter in the lactic acid-based polymer, particularly residual lactide. Alternatively, the residual volatile matter is preferably removed under a pressure of from 0.01 to 50 torr from the material kneaded. Since the lactic acid-based polymer tends to undergo hydrolysis with water content, its kneading is preferably effected under reduced pressure or free from air in an atmosphere of inert gas.

The formation of the biodegradable material of the present invention may be accomplished by any method such as press molding, injection molding and extrusion molding. Alternatively, cutting or polishing may be effected. The biodegradable material thus formed may be subjected to heat treatment so that it is crystallized. The biodegradable material thus crystallized can be provided with a drastically enhanced heat resistance and hardness and tends to exhibit a high stiffness.

The temperature at which the biodegradable material of the present invention is crystallized is from not lower than the glass transition point of the lactic acid-based polymer to not higher than the melting point of the lactic acid-based polymer. In order to accelerate its crystallization, the biodegradable material of the present invention may comprise a nucleating agent such as talc, kaolin, silicon dioxide and boron nitride, crystalline polymer or mixture thereof incorporated therein in an amount of from 0.1 to 10% by weight, preferably from 0.2 to 5% by weight based on the weight of the lactic acid-based polymer. The size of the nucleating agent is not specifically limited. In practice, however, it is preferably from 0.1 to 0.5 $\mu$m.

The biodegradable material of the present invention may comprise various materials incorporated therein depending on the combination of components, i.e., (A) and (B), (A) and (C) or (A) and (B+C). These combinations may be properly selected depending on the purpose. By taking advantage of difference in properties, these combinations are properly combined to form a laminated structure. For example, the combination of (A) and (B) and the combination of (A) and (C) may be combined.

Further, the biodegradable material of the present invention may be used in combination with any other materials such as metal, metal oxide, sintered hydroxyapatite and carbon fiber.

Further, the biodegradable material of the present invention may comprise as a viscosity modifier an alcohol component such as stearyl alcohol, trimethylolethane, trimethylolpropane, pentaerythritol and glycerin incorporated therein in such an amount that the effect of the present invention is not impaired. A known oxidation inhibitor or thermal stabilizer may be added to the reaction system before, during or after polymerization or at the devolatilization step or extrusion step after polymerization. The added amount of these additives is preferably from 0.01 to 5 parts by weight based on 100 parts by weight of the lactic acid-based polyester.

Specific examples of the oxidation inhibitor include 2,6-di-t-butyl-p-cresol, butylated hydroxyanisole, 2,6-di-t-butyl-4-ethylphenol, distearyl 3,3'-thiodipropionate, and dilauryl 3,3'-thiodipropionate. Specific examples of the thermal stabilizer include triphenyl phosphite, trilauryl phosphite, and trinonylphenyl phosphite. Further, a known lubricant or wax may be incorporated in an amount of from 0.01 to 5 parts by weight based on 100 parts by weight of the lactic acid-based polyester.

Examples of the lubricant or wax employable herein include paraffin such as paraffin oil and solid paraffin, higher aliphatic acids such as stearic acid and palmitic acid, higher alcohols such as palmityl alcohol and stearyl alcohol, aliphatic acid metal salts such as calcium stearate, zinc stearate, barium stearate, aluminum stearate, magnesium stearate and sodium palmitate, aliphatic acid esters such as butyl stearate, glycerin monostearate and diethylene glycol monostearate, aliphatic acid amides such as stearamide, methylene bisstearamide, ethylene bisstearamide and ethylenediamide, methylolamide, oleylamide and erucylamide of oxystearic acid, waxes such as carnauba wax and montan wax, and mixture thereof.

The biodegradable material of the present invention exhibits an excellent moldability and thus can cope with various physical properties required. Accordingly, the biodegradable material of the present invention can find wide application as a material which causes little inflammatory reaction. The application is not specifically limited. Specific examples of the application include bone substitute material, material for osteosynthesis, bone filling material, dental material, material having controlled release of chemical, and material having controlled release of physiologically active compound.

The present invention will be further described in the following examples and comparative examples. The term "parts" as used hereinafter is meant to indicate "parts by weight" unless otherwise specified.

The biodegradable materials obtained were evaluated for properties such as moldability, biodegradability, substitutability by fibrous tissue and occurrence of inflammatory reaction.

The molecular weight of the biodegradable materials obtained was measured by GPC in polystyrene equivalence. For the measurement of melting point, a Type DSC-200 differential scanning calorimeter available from Seiko Corp was used. In some detail, melting point was determined from a melting-endothermic curve obtained at a heating rate of 10° C./min. The evaluation of moldability was conducted by means of a melt indexer in accordance with the following 4-step criterion:

E: Extremely excellent in fluidity;
G: Excellent in fluidity;
F: Poor fluidity;
P: No fluidity For the evaluation of biodegradability, the biodegradable material was embedded in dorsal subcutaneous tissue of rats.

After 40 weeks, the difference in molecular weight between the surface layer and the interior was determined. The biodegradability was evaluated in accordance with the following 4-step criterion:

E: The molecular weight of the surface layer is almost the same as that of the interior;

G: The molecular weight of the surface layer is somewhat different from that of the interior;

F: The molecular weight of the surface layer is relatively different from that of the interior;

P: The molecular weight of the surface layer is remarkably different from that of the interior For the evaluation of degree of substitution by fibrous tissue, the biodegradable material was embedded in dorsal subcutaneous tissue of rats. After 40 weeks, the degree of induction and regeneration of fibrous tissue was determined. The degree of substitution by fibrous tissue was evaluated in accordance with the following 4-step criterion:

E: Remarkable induction and regeneration of fibrous tissue;

G: Significant induction and regeneration of fibrous tissue;

F: Traces of induction and regeneration of fibrous tissue;

P: No induction and regeneration of fibrous tissue

For the evaluation of occurrence of inflammatory reaction, the biodegradable material was embedded in dorsal subcutaneous tissue of rats. After 40 weeks, the occurrence of inflammatory reaction in the vicinity of biodegradable material was determined. The occurrence of inflammatory reaction was evaluated in accordance with the following 4-step criterion:

E: No inflammatory reaction observed;

G: Traces of inflammatory reaction observed;

F: Significant inflammatory reaction observed;

P: Remarkable inflammatory reaction observed

REFERENCE EXAMPLE 1

Into a reactor were charged 30 parts of an aliphatic polyester (sebacic acid content: 50 mol-%; propylene glycol content: 50 mol-%; weight-average molecular weight: 46,000), 68 parts of L-lactide, 2 parts of D,L-lactide and 15 parts of toluene as a solvent. These ingredients were then melt-mixed at a temperature of 175° C. in an atmosphere of inert gas for 1 hour. To the reaction mixture was then added 0.03 part of tin octanoate as a catalyst. The reaction mixture was then allowed to undergo reaction at the same temperature for 6 hours. After the termination of the reaction, the resulting lactic acid-based polymer was dissolved in chloroform, precipitated in methanol, filtered, and then devolatilized at 130° C. at 5 torr. The product exhibited a weight-average molecular weight of 156,000 and a melting point of 161° C.

REFERENCE EXAMPLE 2

Into a reactor were charged 10 parts of an aliphatic polyester (succinic acid content: 50 mol-%; 1,4-butanediol content: 50 mol-%; weight-average molecular weight: 39,000), 87 parts of L-lactide, 3 parts of D,L-lactide and 15 parts of toluene as a solvent. These ingredients were then melt-mixed at a temperature of 175° C. in an atmosphere of inert gas for 1 hour. To the reaction mixture was then added 0.03 part of tin octanoate as a catalyst. The reaction mixture was then allowed to undergo reaction at the same temperature for 6 hours. After the termination of the reaction, 10 parts of the resulting lactic acid-based polymer were dissolved in 90 parts of m-cresol. To the solution were then added 100 parts of a 2% aqueous solution of hydrochloric acid. The mixture was stirred for 30 minutes, and then allowed to stand so that an aqueous phase and an organic phase were separated from each other. To the organic phase were then added 100 parts of water. The mixture was stirred, and then allowed to stand so that an organic phase was separated. This procedure was repeated twice. The organic phase was then devolatilized at a temperature of 135° C. at 5 torr. The product exhibited a weight-average molecular weight of 183,000 and a melting point of 162° C.

REFERENCE EXAMPLE 3

Into a reactor were charged 30 parts of an aliphatic polyester (sebacic acid content: 50 mol-%; ethylene glycol content: 50 mol-%; weight-average-molecular weight: 36,000), 70 parts of L-lactide, and 15 parts of toluene as a solvent. These ingredients were then melt-mixed at a temperature of 175° C. in an atmosphere of inert gas for 1 hour. To the reaction mixture was then added 0.03 part of tin octanoate as a catalyst. The reaction mixture was then allowed to undergo reaction at the same temperature for 6 hours. To the reaction mixture were then added 0.1 part of a mixture of monododecyl phosphate and didodecyl phosphate. The reaction mixture was allowed to undergo reaction for 30 minutes, heated to a temperature of 200° C., devolatilized at 5 torr, and then pelletized. The pellet thus. obtained exhibited a weight-average molecular weight of 162,000 and a melting point of 167° C.

REFERENCE EXAMPLE 4

Into a reactor were charged 50 parts of an aliphatic polyester (sebacic acid content: 50 mol-%; 1,6-hexanediol content: 25 mol-%; ethylene glycol content: 25 mol-%; weight-average molecular weight: 36,000), 50 parts of L-lactide, and 15 parts of toluene as a solvent. These ingredients were then melt-mixed at a temperature of 175° C. in an atmosphere of inert gas for 1 hour. To the reaction mixture was then added 0.03 part of tin octanoate as a catalyst. The reaction mixture was then allowed to undergo reaction at the same temperature for 6 hours. To the reaction mixture were then added 0.2 part of ethylenediaminetetraacetic acid. The reaction mixture was allowed to undergo reaction for 30 minutes, heated to a temperature of 200° C., devolatilized at 5 torr, and then pelletized. The pellet thus obtained exhibited a weight-average molecular weight of 147,000 and a melting point of 165° C.

REFERENCE EXAMPLE 5

Into a reactor were charged 5 parts of an aliphatic polyester (sebacic acid content: 50 mol-%; propylene glycol content: 50 mol-%; weight-average molecular weight: 46,000), 68 parts of L-lactide, 2 parts of D,L-lactide, and 15 parts of toluene as a solvent. These ingredients were then melt-mixed at a temperature of 175° C. in anjatmosphere of inert gas for 1 hour. To the reaction mixture was then added 0.03 part of tin octanoate as a catalyst. The reaction mixture was then allowed to undergo reaction at the same temperature for 6 hours. To the reaction mixture were then added 0.1 part of a mixture of mono 2-ethylhexyl phosphate and di-2-ethylhexyl phosphate. The reaction mixture was allowed to undergo reaction for 30 minutes, heated to a temperature of 200° C., devolatilized at 5 torr, and then pelletized. The pellet thus obtained exhibited a weight-average molecular weight of 185,000 and a melting point of 164° C.

REFERENCE EXAMPLE 6

Into a reactor were charged 20 parts of an aliphatic polyester (sebacic acid content: 50mol-%; propylene glycol content: 50 mol-%; weight-average molecular weight: 46,000), 62 parts of L-lactide, 8 parts of D-lactide, and 15 parts of toluene as a solvent. These ingredients were then melt-mixed at a temperature of 175° C. in an atmosphere of inert gas for 1 hour. To the reaction mixture was then added 0.03 part of tin octanoate as a catalyst. The reaction mixture was then allowed to undergo reaction at the same temperature for 6 hours. To the reaction mixture were then added 0.2 part of tartaric acid. The reaction mixture was allowed to undergo reaction for 30 minutes, heated to a temperature of 200° C., devolatilized at 5 torr, and then pelletized. The pellet thus obtained exhibited a weight-average molecular weight of 163,000 and a melting point of 105° C.

EXAMPLE 1

10 parts of the lactic acid-based polymer obtained in Reference Example 1 were dissolved in 90 parts of dioxane. The solution thus obtained was casted into a glass container, immediately cooled to a temperature of 5° C., and then freeze-dried. A 8 mm disc was prepared as an embedding material from the 2 mm thick sheet thus obtained. The disc sample was then embedded in the dorsal subcutaneous tissue of rats. After 40 weeks, the disc sample was taken out from the rats, and then evaluated for molecular weight, biodegradability, degree of substitution by fibrous tissue, occurrence of inflammatory reaction, etc. The results are set forth in Table 1.

EXAMPLE 2

7 parts of the lactic acid-based polymer obtained in Reference Example 1 were dissolved in 90 parts of dioxane. 3 parts of tricalcium phosphate were then dispersed in the solution. The solution thus obtained was casted into a glass container, immediately cooled to a temperature of 5° C., and then freeze-dried. A 8 mm disc was prepared as an embedding material from the 2 mm thick sheet thus obtained. The disc sample was then embedded in the dorsal subcutaneous tissue of rats. After 40 weeks, the disc sample was taken out from the rats, and then evaluated in the same manner as in Example 1. The results are set forth in Table 1.

EXAMPLE 3

7 parts of the lactic acid-based polymer obtained in Reference Example 1 were dissolved in 90 parts of dioxane. 3 parts of a poly(N-vinylpyrrolidone) were then dispersed in the solution. The solution thus obtained was casted into a glass container, immediately cooled to a temperature of 5° C., and then freeze-dried. A 8 mm disc was prepared as an embedding material from the 2 mm thick sheet thus obtained. The disc sample was then embedded in the dorsal subcutaneous tissue of rats. After 40 weeks, the disc sample was taken out from the rats, and then evaluated in the same manner as in Example 1. The results are set forth in Table 1.

EXAMPLE 4

8 parts of the lactic acid-based polymer obtained in Reference Example 2 were dissolved in 90 parts of dichloromethane. 2 parts of hydroxyapatite were then dispersed in the solution. The solution thus obtained was casted into a glass container, and then dried at a temperature of 50° C. at 5 torr. A 8 mm disc was prepared as an embedding material from the 2 mm thick sheet thus obtained. The disc sample was then embedded in the dorsal subcutaneous tissue of rats. After 40 weeks, the disc sample was taken out from the rats, and then evaluated in the same manner as in Example 1. The results are set forth in Table 1.

EXAMPLE 5

5 parts of the lactic acid-based polymer obtained in Reference Example 2 were dissolved in 90 parts of dioxane. 2 parts of tricalcium phosphate, 1 part of a polyethylene glycol and 2 parts of a poly(N-vinylpyrrolidone) were then dispersed in the solution. The solution thus obtained was casted into a glass container, immediately cooled to a temperature of 5° C., and then freeze-dried. A 8 mm disc was prepared as an embedding material from the 2 mm thick sheet thus obtained. The disc sample was then embedded in the dorsal subcutaneous tissue of rats. After 40 weeks, the disc sample was taken out from the rats, and then evaluated in the same manner as in Example 1. The results are set forth in Table 1.

EXAMPLE 6

80 parts of the lactic acid-based polymer obtained in Reference Example 2 and 20 parts of tricalcium phosphate were kneaded in a laboplastomill mixer available from Toyo Seiki K. K. which had been adjusted to 180° C. for 10 minutes, and then taken out. The material thus kneaded was formed by a hot press into a 250 µm thick sheet from which a 8 mm disc was prepared as an embedding sample. The disc sample was then embedded in dorsal subcutaneous tissue of rats. After 40 weeks, the disc sample was taken out from the rats, and then evaluated in the same manner as in Example 1. The results are set forth in Table 2.

EXAMPLE 7

70 parts of the lactic acid-based polymer obtained in Reference Example 3 and 30 parts of tricalcium phosphate were kneaded in a laboplastomill mixer available from Toyo Seiki K. K. which had been adjusted to 180° C. for 10 minutes, and then taken out. The material thus kneaded was formed by a hot press into a 250 µm thick sheet which was then allowed to stand in a 100° C. dryer for 20 minutes for crystallization. A 8 mm disc was prepared as an embedding sample from the sheet. The disc sample was then embedded in dorsal subcutaneous tissue of rats. After 40 weeks, the disc sample was taken out from the rats, and then evaluated in the same manner as in Example 1. The results are set forth in Table 2.

EXAMPLE 8

70 parts of the lactic acid-based polymer obtained in Reference Example 3 and 30 parts of a polyethylene glycol were kneaded in a laboplastomill mixer available from Toyo Seiki K. K. which had been adjusted to 180° C. for 10 minutes, and then taken out. The material thus kneaded was formed by a hot press into a 250 µm thick sheet from which a 8 mm disc was prepared as an embedding sample. The disc sample was then embedded in dorsal subcutaneous tissue of rats. After 40 weeks, the disc sample was taken out from the rats, and then evaluated in the same manner as in Example 1. The results are set forth in Table 2.

EXAMPLE 9

70 parts of the lactic acid-based polymer obtained in Reference Example 4 and 30 parts of hydroxyapatite were kneaded in a laboplastomill mixer available from Toyo Seiki K. K. which had been adjusted to 180° C. for 10 minutes, and then taken out. The material thus kneaded was formed by a hot press into a 250 μm thick sheet which was then allowed to stand in a 100° C. dryer for 20 minutes for crystallization. A 8 mm disc was prepared as an embedding sample from the sheet. The disc sample was then embedded in dorsal subcutaneous tissue of rats. After 40 weeks, the disc sample was taken out from the rats, and then evaluated in the same manner as in Example 1. The results are set forth in Table 2.

EXAMPLE 10

70 parts of the lactic acid-based polymer obtained in Reference Example 4 and 30 parts of a polyethylene glycol were kneaded in a laboplastomill mixer available from Toyo Seiki K. K. which had been adjusted to 180° C. for 10 minutes, and then taken out. The material thus kneaded was formed by a hot press into a 250 μm thick sheet which was then allowed to stand in a 100° C. dryer for 20 minutes for crystallization. A 8 mm disc was prepared as an embedding sample from the sheet. The disc sample was then embedded in dorsal subcutaneous tissue of rats. After 40 weeks, the disc sample was taken out from the rats, and then evaluated in the same manner as in Example 1. The results are set forth in Table 2.

EXAMPLE 11

70 parts of the lactic acid-based polymer obtained in Reference Example 4, 20 parts of a polyethylene glycol and 10 parts of calcium phosphate were kneaded in a laboplastomill mixer available from Toyo Seiki K. K. which had been adjusted to 180° C. for 10 minutes, and then taken out. The material thus kneaded was formed by a hot press into a 250 μm thick sheet which was then allowed to stand in a 100° C. dryer for 20 minutes for crystallization. A 8 mm disc was prepared as an embedding sample from the sheet. The disc sample was then embedded in dorsal subcutaneous tissue of rats. After 40 weeks, the disc sample was taken out from the rats, and then evaluated in the same manner as in Example 1. The results are set forth in Table 3.

EXAMPLE 12

90 parts of the lactic acid-based polymer obtained in Reference Example 5 and 10 parts of tricalcium phosphate were kneaded in a laboplastomill mixer available from Toyo Seiki K. K. which had been adjusted to 180° C. for 10 minutes, and then taken out. The material thus kneaded was formed by a hot press into a 250 μm thick sheet which was then allowed to stand in a 100° C. dryer for 20 minutes for crystallization. A 8 mm disc was prepared as an embedding sample from the sheet. The disc sample was then embedded in dorsal subcutaneous tissue of rats. After 40 weeks, the disc sample was taken out from the rats, and then.evaluated in the same manner as in Example 1. The results are set forth in Table 3.

EXAMPLE 13

70 parts of the lactic acid-based polymer obtained in Reference Example 6, 10 parts of tricalcium phosphate, 10 parts of a polyethylene glycol and 10 parts of a poly(N-vinylpyrrolidone) were kneaded in a laboplastomill mixer available from Toyo Seiki K. K. which had been adjusted to 110° C. for 10 minutes, and then taken out. The material thus kneaded was formed by a hot press into a 250 μm thick sheet which was then allowed to stand in a 100° C. dryer for 20 minutes for crystallization. A 8 mm disc was prepared as an embedding sample from the sheet. The disc sample was then embedded in dorsal subcutaneous tissue of rats. After 40 weeks, the disc sample was taken out from the rats, and then evaluated in the same manner as in Example 1. The results are set forth in Table 3.

COMPARATIVE REFERENCE EXAMPLE 1

Into a reactor were charged 95 parts of L-lactide, 5 parts of D,L-lactide and 15 parts of toluene as a solvent. These ingredients were then melt-mixed at a temperature of 175° C. in an atmosphere of inert gas for 1 hour. To the reaction mixture was then added 0.03 part of tin octanoate as a catalyst. The reaction mixture was allowed to undergo reaction at the same temperature for 6 hours, heated to a Atemperature of 200° C., devolatilized at 5 torr, and then pelletized. The product exhibited a weight-average molecular weight of 143,000.

COMPARATIVE REFERENCE EXAMPLE 2

Into a reactor were charged 96 parts of L-lactide, 2 parts of D-lactide, 2 parts of glycolide and 15 parts of toluene as a solvent. These ingredients were then melt-mixed at a temperature of 175° C. in an atmosphere of inert gas for 1 hour. To the reaction mixture was then added 0.03 part of tin octanoate as a catalyst. The reaction mixture was allowed to undergo reaction at the same temperature for 6 hours, heated to a temperature of 200° C., devolatilized at 5 torr, and then pelletized. The product exhibited a weight-average molecular weight of 138,000.

COMPARATIVE EXAMPLE 1

The polylactic acid obtained in Comparative Reference Example 1 was formed by a hot press into a 250 μm thick sheet. A 8 mm disc was prepared as an embedding sample from the sheet. The disc sample was then embedded-in dorsal subcutaneous tissue of rats. After 40 weeks, the disc sample was taken out from the rats, and then evaluated in the same manner as in Example 1. The results are set forth in Table 4.

COMPARATIVE EXAMPLE 2

70 parts of the polylactic acid obtained in Comparative Reference Example 1 and 30 parts of tricalcium phosphate were kneaded in a laboplastomill mixer available from Toyo Seiki K. K. which had been adjusted to 180° C. for 10 minutes, and then taken out. The material thus kneaded was formed by a hot press into a 250 μm thick sheet. A 8 mm disc was prepared as an embedding sample from the sheet. The disc sample was then embedded in dorsal subcutaneous tissue of rats. After 40 weeks, the disc sample was taken out from the rats, and then evaluated in the same manner as in Example 1. The results are set forth in Table 4.

COMPARATIVE EXAMPLE 3

70 parts of the polylactic acid obtained in Comparative Reference Example 2 and 20 parts of hydroxyapatite were kneaded in a laboplastomill mixer available from Toyo Seiki K. K. which had been adjusted to 180° C. for 10 minutes, and then taken out. The material thus kneaded was formed by a hot press into a 250 μm thick sheet which was then allowed to stand in a 100° C. dryer for 20 minutes for crystallization. A 8 mm disc was prepared as an embedding sample from the sheet. The disc sample was then embedded in dorsal subcutaneous tissue of rats. After 40 weeks, the disc sample was taken out from the rats, and then evaluated in the same manner as in Example 1. The results are set forth in Table 4.

TABLE 1

|  | Example No. | | | | |
| --- | --- | --- | --- | --- | --- |
|  | 1 | 2 | 3 | 4 | 5 |
| Moldability | E | E | E | E | E |
| Biodegradability | E | E | E | E | E |
| Degree of substitution by fibrous tissue | F | E | E | E | E |
| Occurrence of inflammatory reaction | G | E | E | E | E |

TABLE 2

|  | Example No. | | | | |
| --- | --- | --- | --- | --- | --- |
|  | 6 | 7 | 8 | 9 | 10 |
| Moldability | E | E | E | E | E |
| Biodegradability | E | E | E | E | E |
| Degree of substitution by fibrous tissue | F | G | E | G | E |
| Occurrence of inflammatory reaction | E | E | G | E | G |

TABLE 3

|  | Example No. | | |
| --- | --- | --- | --- |
|  | 11 | 12 | 13 |
| Moldability | E | E | E |
| Biodegradability | E | E | E |
| Degree of substitution by fibrous tissue | E | G | E |
| Occurrence of inflammatory reaction | E | E | E |

TABLE 4

|  | Comparative Example No. | | |
| --- | --- | --- | --- |
|  | 1 | 2 | 3 |
| Moldability | F | F | F |
| Biodegradability | F | F | F |
| Degree of substitution by fibrous tissue | F | F | F |
| Occurrence of inflammatory reaction | E | E | E |

As mentioned above, the present invention provides a biodegradable material such as bone substitute material, material for osteosynthesis, dental material and material having controlled release of chemical comprising as an essential component a lactic acid-based polymer consisting of structural units derived from lactic acid components and polyester structural units derived from dicarboxylic acid components and diol components which exhibits an excellent moldability and controlled biodegradability and allows an excellent regeneration of tissues. The present invention also provides a process for the preparation of such a biodegradable material.

While the invention has been described in detail and with reference to specific embodiments thereof, it will be apparent to one skilled in the art that various changes and modifications can be made therein without departing from the spirit and scope thereof.

What is claimed is:

1. A biodegradable material, comprising as essential components a lactic acid-based polymer (A) consisting of structural units (a) derived from lactic acid components and polyester structural units (b) derived from dicarboxylic acid components and diol components, the weight ratio of (a)/(b) being from 98/2 to 20/80, and a calcium phosphate-based compound (B), wherein the weight ratio of (A)/(B) is from 99/1 to 30/70.

2. A process for the preparation of a biodegradable material, which comprises kneading a lactic acid-based polymer (A) consisting of structural units (a) derived from lactic acid components and polyester structural units (b) derived from dicarboxylic acid components and diol components, the weight ratio of (a)/(b) being from 98/2 to 20/80, and a calcium phosphate-based compound (B) at a temperature of not lower than the melting point of said lactic acid-based polymer (A) in such an amount that the weight ratio (A)/(B) is from 99/1 to 30/70.

* * * * *